United States Patent
Wantink

(10) Patent No.: US 6,746,423 B1
(45) Date of Patent: Jun. 8, 2004

(54) CATHETER HAVING IMPROVED RAPID EXCHANGE JUNCTION

(75) Inventor: Kenneth L. Wantink, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 209 days.

(21) Appl. No.: 10/002,477

(22) Filed: Nov. 1, 2001

(51) Int. Cl.[7] .................. A61M 29/00; A61M 31/00; A61M 37/00
(52) U.S. Cl. ............... 604/103.04; 604/96.01; 606/194
(58) Field of Search .............. 604/96.01, 103.04, 604/103.05, 103.06, 103.08, 103.11, 103.12, 103.09, 102.01, 102.02, 102.03, 528; 606/192–196

(56) References Cited

U.S. PATENT DOCUMENTS

| | | | |
|---|---|---|---|
| 5,061,273 A | | 10/1991 | Yock |
| 5,156,594 A | | 10/1992 | Keith |
| 5,496,275 A | | 3/1996 | Sirhan et al. |
| 5,533,968 A | * | 7/1996 | Muni et al. ............ 604/103.11 |
| 5,554,121 A | | 9/1996 | Ainsworth et al. |
| 6,179,810 B1 | * | 1/2001 | Wantink et al. .......... 604/96.01 |
| 6,193,686 B1 | * | 2/2001 | Estrada et al. ......... 604/103.09 |
| 6,344,029 B1 | * | 2/2002 | Estrada et al. ......... 604/103.09 |
| 6,589,226 B1 | * | 7/2003 | Owens .................. 604/523 |

FOREIGN PATENT DOCUMENTS

| | | |
|---|---|---|
| WO | WO 93/20882 | 10/1993 |
| WO | WO 01/89621 A1 | 11/2001 |

OTHER PUBLICATIONS

U.S. Publication No.: 2001/0029362 A1; Motasim M. Sirhan, et al., Catheter Shaft with an Oblong Transverse Cross–Section, Publication Date Oct. 11, 2001.

* cited by examiner

Primary Examiner—Brian L. Casler
Assistant Examiner—Michael M Thompson
(74) Attorney, Agent, or Firm—Fulwider Patton Lee & Utecht, LLP

(57) ABSTRACT

A balloon catheter, and preferably to a rapid exchange type balloon catheter, having a proximal shaft section, and a distal shaft section with an inner tubular member and an outer tubular member, the outer tubular member having a section which is bonded as by fusing or otherwise bonding. The bonded section extends along a thickened wall portion of the outer tubular member at the rapid exchange junction. A reinforcing member or tube extends within at least a section of the bonded section of the outer tubular member. In one embodiment, the reinforcing tube extends within at least a section of the thickened wall portion of the outer tubular member. The configuration provides a rapid exchange junction with improved kink resistance and flexibility for excellent trackability, and with a minimal decrease in the size of the inflation lumen at the rapid exchange junction for an improved shortened balloon inflation/deflation time.

3 Claims, 4 Drawing Sheets

CATHETER HAVING IMPROVED RAPID EXCHANGE JUNCTION

BACKGROUND OF THE INVENTION

This invention generally relates to catheters, and particularly intravascular catheters for use in percutaneous transluminal coronary angioplasty (PTCA) or for the delivery of stents.

In a typical PTCA procedure, a dilatation balloon catheter is advanced over a guidewire to a desired location within the patient's coronary anatomy, to position the balloon of the dilatation catheter within the stenosis to be dilated. The balloon is then inflated with radiopaque liquid at relatively high pressures (generally 4–16 atmospheres) to dilate the stenosed region of the diseased artery. One or more inflations may be needed to effectively dilate the stenosis. Additionally, a stent may be implanted within the artery, typically by delivery to a desired location within the artery in a contracted condition on a balloon of a catheter which is similar in many respects to a balloon angioplasty catheter and expansion to a larger diameter by inflation of the balloon.

In rapid exchange type balloon catheters, the catheter has an inflation lumen extending from the proximal end of the catheter to a balloon on a distal shaft section, a distal guidewire port at the distal end of the catheter, a proximal guidewire port located distal to the proximal end of the catheter, and a relatively short guidewire lumen extending therebetween. The distal shaft section defines the guidewire lumen, and a distal portion of the inflation lumen in fluid communication with the proximal portion of the inflation lumen defined by the single lumen proximal shaft section. The rapid exchange junction located at the proximal guidewire port at the transition between the proximal shaft section and the distal shaft section should provide a good transition in flexibility from the relatively stiff proximal shaft section to the relatively flexible distal shaft section to facilitate tracking the catheter within the patient's tortuous vasculature. One difficulty has been forming a rapid exchange junction with the desired characteristics of flexibility, kink resistance, and pushability (i.e., the ability to transmit force from the proximal end to the distal end of the catheter).

To help meet the desire for a catheter having sufficient pushability and crossability, while maintaining trackability, prior art designs have supplemented polymer catheter shafts with a support mandrel. Other prior art designs have addressed these handling and performance issues by using materials of different stiffness for the proximal and distal portions of the catheter, and employing a high strength metallic proximal shaft section, commonly called a hypotube. To prevent kinking at the junction of these two materials, while maintaining trackability and pushability, some conventional designs have employed reinforcing layers or stiffening wires to bridge the transition in catheter shaft material. Despite these attempts, prior art designs have suffered from various drawbacks relating to these handling and performance issues.

Accordingly, it would be a significant advance to provide a catheter having an improved rapid exchange junction.

SUMMARY OF THE INVENTION

The invention is directed to a balloon catheter, and preferably to a rapid exchange type balloon catheter, having a proximal shaft section, and a distal shaft section with an inner tubular member and an outer tubular member, the outer tubular member having a section which is bonded as by fusing or otherwise bonding (i.e., "the bonded section") to the inner tubular member. The bonded section extends along a thickened wall portion of the outer tubular member at the rapid exchange junction. A reinforcing member or tube extends within at least a section of the bonded section of the outer tubular member. In one embodiment, the reinforcing tube extends within at least a section of the thickened wall portion of the outer tubular member. The configuration provides a rapid exchange junction with improved kink resistance and flexibility for excellent trackability, and with a minimal decrease in the size of the inflation lumen at the rapid exchange junction for an improved shortened balloon inflation/deflation time.

The balloon catheter of the invention generally comprises an elongated shaft having the proximal shaft section and distal shaft section, an inflation lumen, a guidewire receiving lumen extending in the distal shaft section, and a balloon on the distal shaft section with an interior in fluid communication with the inflation lumen. The proximal shaft section defines a proximal portion of the inflation lumen, and is preferably a metallic tubular member such as a hypotube, although high strength polymers such as polyetheretherketone (PEEK), and polyamide may alternatively be used. The outer tubular member of the distal shaft section defines a distal portion of the inflation lumen in fluid communication with the proximal shaft section and the balloon. The inner tubular member within the distal portion of the inflation lumen defines the guidewire lumen in fluid communication with a guidewire distal port at the inner tubular member distal end and a guidewire proximal port at the inner tubular member proximal end.

As a rapid exchange type catheter, the proximal guidewire port is located in the distal shaft section, distal to the proximal end of the catheter shaft, and preferably a relatively short distance from the balloon and a relatively long distance from the proximal end of the catheter. The proximal guidewire port at the rapid exchange junction is formed by placing the inner tubular member through a hole cut in the outer tubular member side wall, and then bonding part of the circumference of the inner tubular member to the outer tubular member to form the bonded section. The bonded section forms the transition between the single lumen proximal portion of the shaft, and the distal portion of the shaft having the guidewire lumen and the distal portion of the inflation lumen.

In a presently preferred embodiment, the bonded section is formed by thermally bonding (i.e., fusing) the inner tubular member to the outer tubular member by applying heat to melt the polymeric material and fuse the members together. However, the bonded section can be formed by adhesively bonding or a combination of adhesively bonding and thermally bonding the inner and outer members together. Although discussed below primarily in terms of the preferred, fusion bonded embodiment in which the bonded section consists of a fused section, it should be understood that the discussion below also applies to the embodiments in which the bonded section is formed in whole or in part by methods other than fusion bonding. In a presently preferred embodiment, the fused section has a relatively short length, which, in one embodiment, extends from the proximal end of the inner tubular member to a location proximal to the distal end of the outer tubular member. The fused section is preferably formed by locally applying the heat in a focused manner to just the portion of the shaft extending from the guidewire proximal port distally about 1 cm or less. In a presently preferred embodiment, the fused section has a length of about 0.1 to about 1 cm. As a result, the transition formed by the fused section at the rapid exchange junction provides a minimal decrease in the overall size of the inflation lumen as a result of the junction, to thereby minimize the balloon inflation/deflation times.

The thickened wall portion of the outer tubular member is fused to the inner tubular member to form at least a portion of the fused section of the outer tubular member. The thickened wall portion has an inner periphery with a first segment which is bonded to part of an outer surface of the inner tubular member and which extends around part of the inner periphery of the thickened wall portion, and a second segment which is not bonded to the inner tubular member and which extends around the remaining part of the inner periphery of the thickened wall portion of the outer tubular member. In one embodiment, about 10% to about 95%, preferably about 10% to about 70%, and more specifically about 10% to about 50% of an outer periphery (extending around part of the circumference) of the inner tubular member is bonded to the thickened wall portion of the outer tubular member to form the first segment of the inner periphery of the thickened wall portion (i.e., it extends around about 36 to about 320 degrees, preferably about 36 to about 250 degrees of a 360° outer periphery of the inner tubular member).

The reinforcing tube within the fused section extends within the outer tubular member of the distal shaft section without necessarily being bonded, e.g., fused or adhesively bonded, thereto. For example, the reinforcing tube can be friction fit within the outer tubular member. Alternatively, part or all of the length of the reinforcing tube can be bonded to the outer tubular member. In one embodiment, at least the distal end of the reinforcing tube is not bonded to the distal outer tubular member, for increased flexibility at the rapid exchange junction. The reinforcing tube is preferably formed of a polymeric material selected from the group consisting of PEEK, polyimide, and other high modulus engineering thermoplastic/thermoset polymers such as polytetrafluoroethylene (PTFE), e.g., TEFLON. The inflation lumen extending within the thickened wall portion of the outer tubular member may be defined by the reinforcing tube extending therein, in which case the second segment of the inner periphery of the outer tubular member thickened wall portion is in contact with the reinforcing tube. In an alternative embodiment, the inflation lumen extending within the thickened wall portion of the outer tubular member is defined by the thickened wall portion itself, in which case the distal end of the reinforcing tube is located proximal to the distal end of the thickened wall portion of the outer tubular member.

The thus formed distal shaft section provides a distal subassembly which can be attached to any type of proximal shaft section, typically by adhesive or fusion bonding the proximal end of the outer tubular member to the distal end of a desired proximal shaft section. In one embodiment, the proximal end of the outer tubular member and the reinforcing tube therein are bonded to the distal end of the proximal shaft section.

The catheter of the invention has excellent ability to track within the patient's tortuous vasculature due to the improved rapid exchange junction. The fused section of the outer tubular member, with at least a section of the reinforcing tube extending therein and formed at least in part by the thickened wall portion of the outer tubular member, provides a rapid exchange junction with high pushability and flexibility. Moreover, the rapid exchange junction has a short length, which consequently provides for an improved, minimized inflation/deflation duration. These and other advantages of the invention will become more apparent from the following detailed description and drawings.

DETAILED DESCRIPTION OF THE INVENTION

Figure 1:
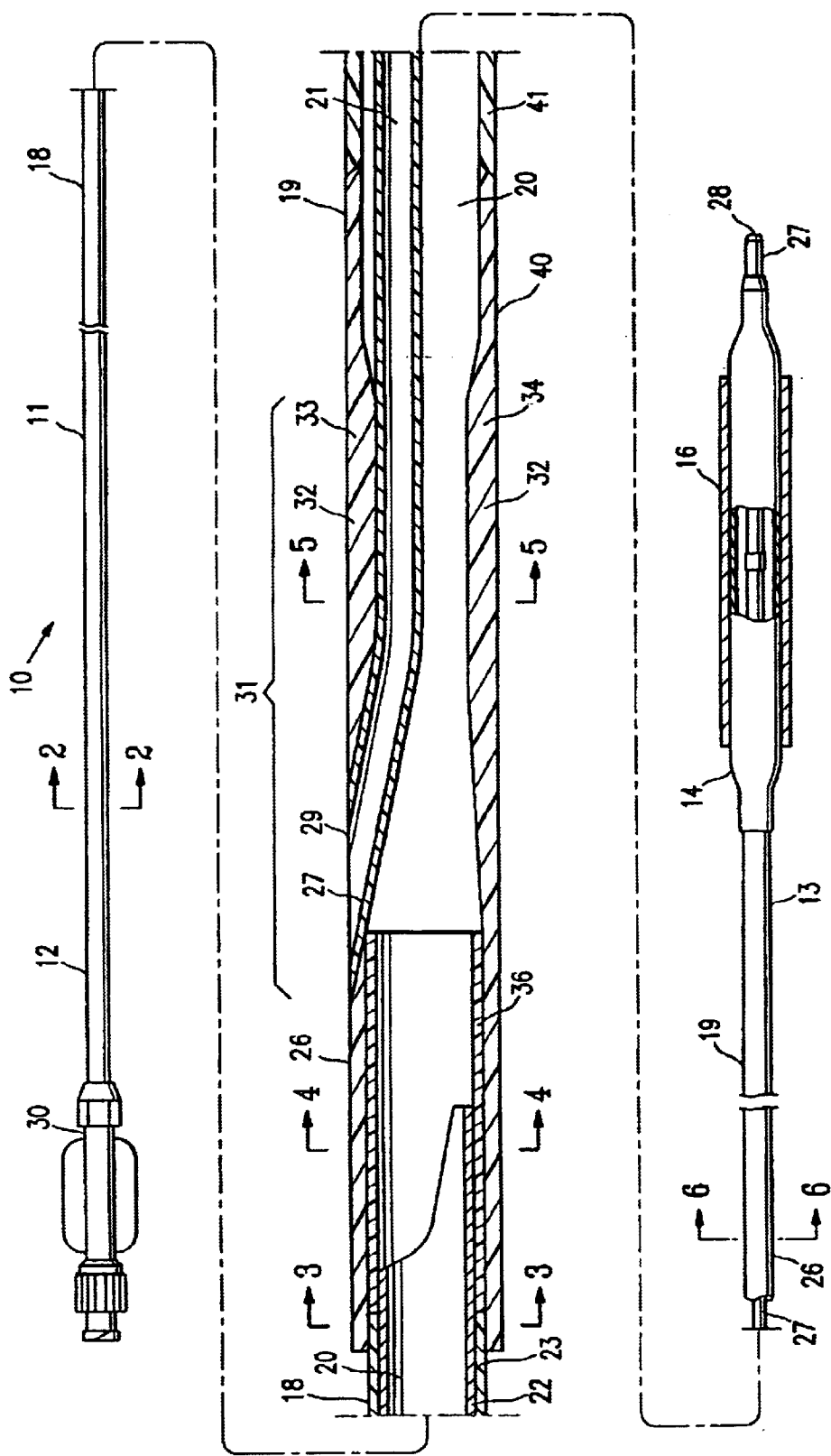
FIG. 1 is an elevational view, partially in section, of a rapid exchange balloon catheter which embodies features of the invention.
Figure 2:
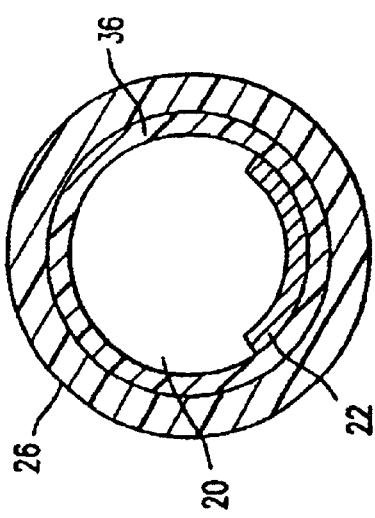
FIG. 2 is a transverse cross sectional view of the catheter shown in FIG. 1, taken along line 2—2.
Figure 3:
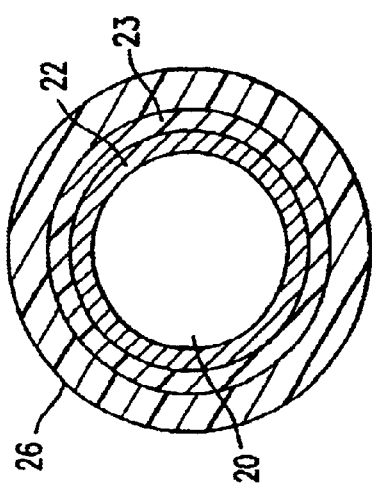
FIG. 3 is a transverse cross sectional view of the catheter shown in FIG. 1, taken along line 3—3.
Figure 4:
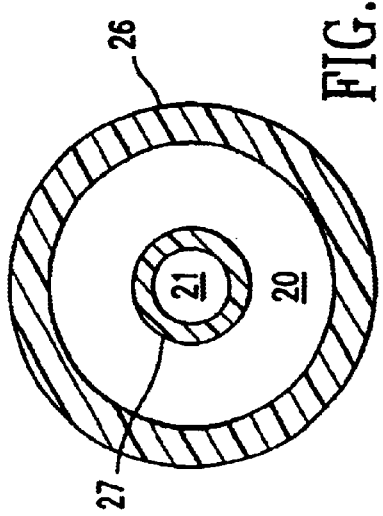
FIG. 4 is a transverse cross sectional view of the catheter shown in FIG. 1, taken along line 4—4.

FIG. 1 illustrates rapid exchange type stent delivery balloon catheter 10 embodying features of the invention. Catheter 10 generally comprises an elongated catheter shaft 11 having a proximal end 12, a distal end 13, and an inflatable balloon 14 on a distal shaft section. An expandable tubular stent 16 is mounted on balloon 14 for implanting in the patient's body lumen. The shaft 11 has a proximal shaft section 18, a distal shaft section 19 at the distal end of the proximal shaft section, an inflation lumen 20, and a guidewire receiving lumen 21. The proximal shaft section 18 comprises a high strength tubular member 22 which is preferably a metallic tubular member such as a stainless steel or NiTi tubular member. In the embodiment illustrated in FIG. 1, a polymeric outer layer 23 is provided on the outer surface of the metallic tubular member 22. Polymeric outer layer 23 is preferably formed of a coextrusion of polyether block amide (PEBAX) and adhesive polymer such as Primacor, although a variety of suitable polymeric materials can be used including nylon and polyurethane. The metallic tubular member 22 defines a proximal portion of the inflation lumen 20. The distal end of the metallic tubular member 22 tapers distally to a smaller transverse dimension, as is conventional in the design of proximal catheter shafts formed of a hypotube. FIGS. 2–4 illustrate transverse cross sections of the catheter of FIG. 1, taken along the length of the metallic tubular member 22 along lines 2—2, 3—3, and 4—4, respectively. In the embodiment illustrated in FIG. 4, the tapered portion of the metallic tubular member 22 has a C-shaped cross section extending only partially around the circumference of the shaft. The distal shaft section 19 comprises an outer tubular member 26 defining a distal portion of the inflation lumen 20, and an inner tubular member 27 defining the guidewire lumen 21 in fluid communication with a guidewire distal port 28 at the distal end of the inner tubular member 27 and a guidewire proximal port 29 at the proximal end of the inner tubular member 27. In the embodiment of FIG. 1, the distal shaft section 19 and the proximal shaft section 18 overlap at their proximal and distal ends, respectively, to form a lap joint. A rapid exchange junction at the guidewire proximal port 29 is the transition between the single lumen proximal shaft section and the multilumen distal shaft section. An adapter 30 at the proximal end of the catheter provides access to the inflation lumen 20. Balloon 14 has a proximal end sealingly secured to the distal end of outer tubular member 26 and a distal end sealingly secured to the distal end of inner tubular member 27, so that its interior is in fluid communication with inflation lumen 20. The distal end of catheter may be advanced to a desired region of a patient's body lumen in a conventional manner and balloon 14 inflated to expand stent 16. The catheter 10 is withdrawn after deflating the balloon 14, leaving the implanted stent 16 in the body lumen.

Figure 5:
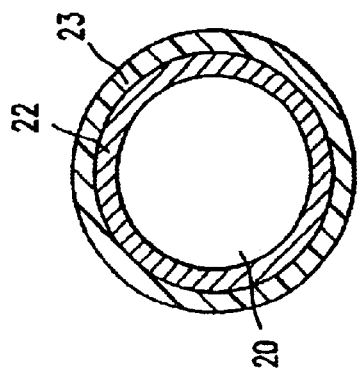
FIG. 5 is a transverse cross sectional view of the catheter shown in FIG. 1, taken along line 5—5.
Figure 6:
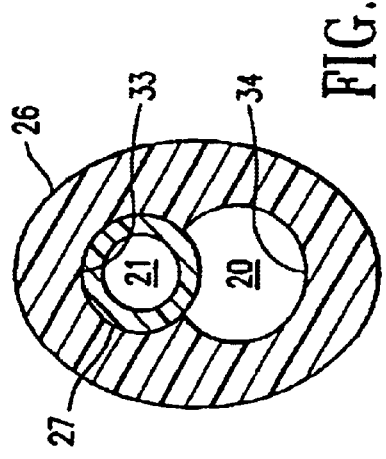
FIG. 6 is a transverse cross sectional view of the catheter shown in FIG. 1, taken along line 6—6.

A bonded section 31 of the outer tubular member is bonded to the inner tubular member, preferably by fusion bonding (hereafter "the fused section 31"). The fused section 31 extends from the proximal end of the inner tubular member 27 to a location proximal to the distal end of the outer tubular member 26, which in the embodiment of FIG. 1 is spaced proximally from the proximal end of the balloon 14. In a presently preferred embodiment, the fused section 31 has a length of about 1 to about 10 mm, and more specifically about 5 to about 7 mm, and is about 0.3 to about 0.6% of the total length of the catheter shaft. In the embodiment of FIG. 1, the section of the inner tubular member 27 distal to the fused section 31 is disposed in the outer tubular member lumen without being fused thereto, which provides a flexible distal shaft section with a minimal decrease in the inflation lumen area. The proximal section of the inner tubular member 27 is eccentrically disposed in the outer tubular member lumen, as best illustrated in FIG. 5, showing a transverse cross section of the catheter 10 of FIG. 1, taken along line 5—5. The distal section of the inner tubular member 27 is coaxially disposed in the outer tubular member lumen, as best illustrated in FIG. 6, showing a transverse cross section of the catheter of FIG. 1, taken along line 6—6.

The outer tubular member 26 has a thickened wall portion 32 in the fused section 31. In the embodiment of FIG. 1, the thickened wall portion 32 of the outer tubular member 26 is located distal to the guidewire proximal port 29, although in an alternative embodiment (not shown) it may have a proximal end located proximal to the guidewire proximal port 29. In a presently preferred embodiment, the thickened wall portion 32 has a length of about 1 to about 10 mm, and more specifically about 5 to about 7 mm. The thickened wall portion 32 has an inner periphery with a first segment 33 which is fused to part of an outer surface of the inner tubular member 27, and a second segment 34 which is not fused to the inner tubular member. The first segment 33 extends around part of the inner periphery of the thickened wall portion 32, and the second segment 34 extends around the remaining part of the periphery of the inner periphery of the thickened wall portion 32 radially adjacent to the first segment. In the embodiment illustrated in FIG. 5, about 70% of the outer surface of the inner tubular member 27 is bonded to the thickened wall portion 32, to form the first segment 33 of the inner periphery of the outer tubular member 26 thickened wall portion 32.

A reinforcing tube 36 extends within at least a section of the fused section 31 of the outer tubular member 26 (i.e., the reinforcing tube 36 distal end is distal to the proximal end of the fused section 31). The reinforcing tube 36 is preferably formed of a relatively high strength polymeric material which provides the rapid exchange junction at the guidewire proximal port 29 with more flexibility than the metallic tubular member 22 of the proximal shaft section 18. In a presently preferred embodiment, the reinforcing tube 36 is formed of PEEK. In the embodiment illustrated in FIG. 1, the distal end of the reinforcing tube 36 is located at the proximal end of the thickened wall portion 32 of the outer tubular member 26, at the guidewire proximal port 29, although in alternative embodiments, it may be located distal thereto. With the distal end of the reinforcing tube 36 proximal to the distal end of the thickened wall portion of the outer tubular member 26, the inflation lumen 20 extending within the thickened wall portion 32 of the outer tubular member 26 is defined by the thickened wall portion 32.

The distal shaft section 19 comprises a subassembly which can be joined to a variety of proximal shaft sections by bonding the proximal end of the outer tubular member 26 to the proximal shaft section. The subassembly is formed by positioning the distal end of the inner tubular member 27 in a hole or port in the side wall of the outer tubular member 26. A mandrel (not shown), which has a distal end tapering to a smaller diameter along side the inner tubular member 27, is positioned in the inflation lumen, to keep the inflation lumen open during the fusing of the inner and outer tubular members. The subassembly is completed by applying heat to fuse the inner and the outer tubular members 27/26 together and form the fused section 31. During the fusing, the polymeric material forming the outer tubular member 26 flows and fills in around the tapered mandrel to thereby form the thickened wall portion 32 of the outer tubular member 26. In the embodiment illustrated in FIG. 5, the fused section 31 has an oval or elliptical transverse cross section as a result of the fusing process. The inflation lumen 20 thus tapers to a smaller diameter in the fused section 31 of the outer tubular member 26, however, because the length of the fused section 31 is minimized, the effect on the inflation/deflation time of the catheter 10 is minimized. The tapered mandrel is then removed and the distal shaft section 19 secured to the proximal shaft section 18 to complete the shaft assembly. In the embodiment of FIG. 1, the distal end of the metallic tubular member 22 is positioned within the reinforcing tube 36, and the proximal end of the reinforcing tube 36 is bonded by gluing with an adhesive to the distal end of the metallic tubular member 22. The distal end of the reinforcing tube 36 is positioned within the outer tubular member 26, into contact therewith and, in a presently preferred embodiment, not bonded thereto. The proximal end of the outer tubular member 26 is then bonded to the distal end of the proximal shaft section 18, as in the embodiment of FIG. 1, by fusion or adhesively bonding to the polymeric outer layer 23 of the metallic tubular member 22.

In a presently preferred embodiment, the outer tubular member 26 comprises a first section 40 formed of a first polymeric material, and a second section 41 bonded to the distal end of the first section 40 and formed of a second polymeric material different from the first polymeric material. The second polymeric material preferably is fusion bondable to the polymeric material of the balloon 14, and may have a lower Shore Durometer hardness than the first polymeric material. The first polymeric material is preferably a polyamide such as nylon 12, however a variety of suitable materials may be used including polyether block amide (PEBAX) and polyurethane. The second polymeric material is preferably a polyamide copolymer such as PEBAX, and specifically PEBAX 72D, available from Autochem, however a variety of suitable materials may be used including polyurethane and nylon. In the embodiment of FIG. 1, the distal end of the thickened wall portion 32 of the outer tubular member is located proximal to the second section 41 of the outer tubular member, so that the first section 40 of the outer tubular member comprises the thickened wall portion 32 and portions on either end of the thickened wall portion having a smaller wall thickness than the thickened wall section. Similarly, the distal end of the fused section 31 of the outer tubular member is located proximal to the second section 41 of the outer tubular member.

Figure 7:
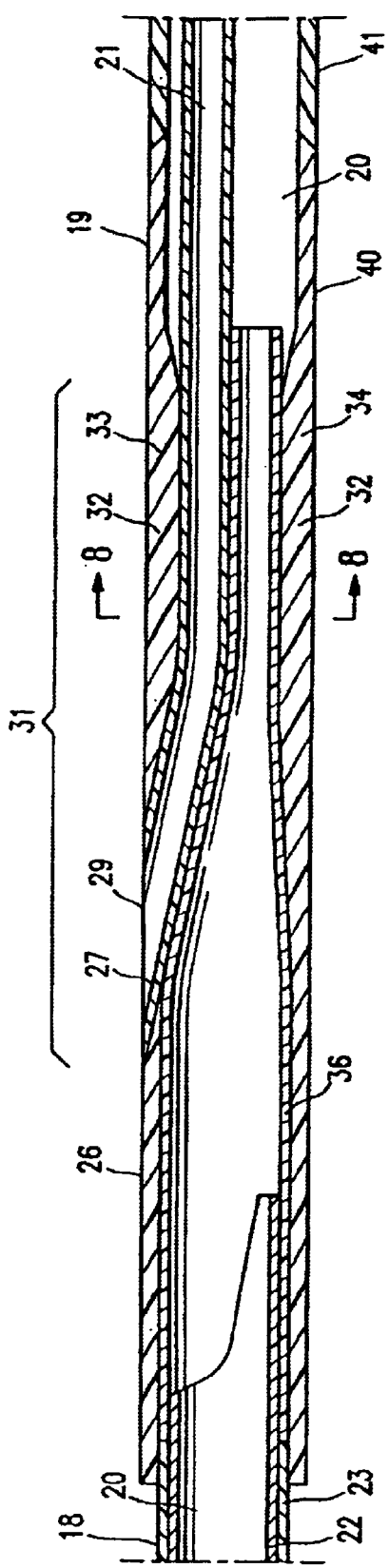
FIG. 7 is a longitudinal cross sectional view of an of an alternative rapid exchange junction which embodies features of the invention, having a reinforcing tube extending within a thickened wall section of the outer tubular member.
Figure 8:
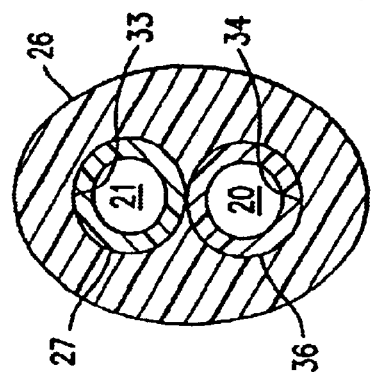
FIG. 8 is a transverse cross sectional view of the catheter shown in FIG. 7, taken along line 8—8.

FIG. 7 illustrates an alternative embodiment, in which the reinforcing tube 36 extends within at least a section of the thickened wall portion 32 of the outer tubular member 26 to a location along the length of the thickened wall portion 32 or alternatively to a location distal to the thickened wall portion 32. In the embodiment of FIG. 7, the distal end of the reinforcing tube 36 is at the distal end of the thickened wall portion 32. The reinforcing tube 36 distal end is typically necked or otherwise reduced in diameter to extend within the smaller inner diameter of the thickened wall portion 32. Preferably, the reduced diameter distal section of the reinforcing tube 36 is not fused or otherwise bonded to the outer tubular member 26, for added flexibility. In the embodiment of FIG. 7, about 90% to about 95% of the outer surface of the inner tubular member 27 is bonded to the inner periphery of the thickened wall portion 32 of the outer tubular member 26, to form the first segment 33 of the inner periphery of the outer tubular member 26 thickened wall portion 32, as best illustrated in FIG. 8 showing a transverse cross section of the catheter of FIG. 7, taken along line 8—8. As with the embodiment of FIG. 1, the second segment 34 of the outer tubular member 26 is not bonded to the inner tubular member 27, although it may be at least in part bonded to the reinforcing tube 36 extending therein. With the distal end of the reinforcing tube 36 located at the distal end of the thickened wall portion 32 of the outer tubular member 26, the inflation lumen 20 extending within the thickened wall portion 32 is defined by the reinforcing tube 36 extending therein, and the second segment 34 of the inner periphery of the thickened wall portion 32 of the outer tubular member 26 is in contact with the reinforcing tube 36.

Figure 9:
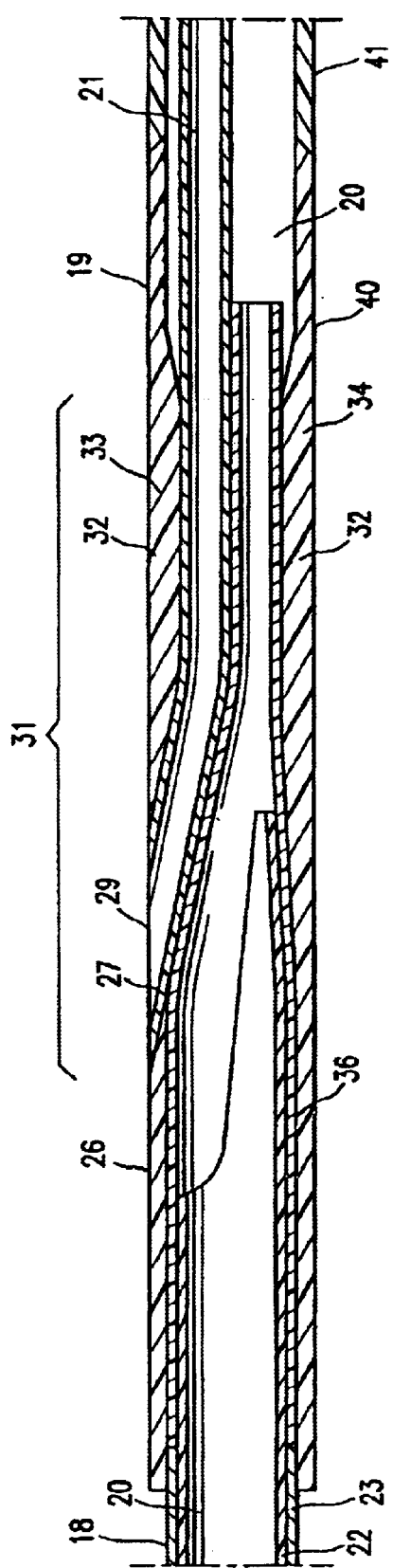
FIG. 9 is a longitudinal cross sectional view of an of an alternative rapid exchange junction which embodies features of the invention, having the distal end of the proximal shaft section hypotube distal to the proximal guidewire port.

FIG. 9 illustrates an alternative embodiment of the invention, in which the metallic tubular member 22 has a distal end located distal to the proximal guidewire port 29. In the embodiment illustrated in FIG. 9, the reinforcing tube 36 extends to a location distal to the thickened wall portion 32. The distal end of the reinforcing tube 36 is preferably proximal to the second section 41 of the outer tubular member 26, and specifically, the distal end of the reinforcing tube 36 is preferably about 5 mm or less from the distal end of the thickened wall portion 32.

The catheter shaft will generally have the dimensions of conventional dilatation or stent delivery catheters. The length of the catheter 10, measured from the distal end of the adapter 30 to the distal end of the catheter is about 90 to about 150 cm, typically about 143 cm. The metallic tubular member 22 of the proximal shaft section 18 has a length of about 110 to about 115 cm, typically about 114 cm, an outer diameter (OD) of about 0.025 to about 0.02 inches, and an inner diameter (ID) of about 0.015 to about 0.0185 inches. The outer tubular member 26 of the distal shaft section 19 has a length of about 15 to about 25 cm, typically about 23 cm, an OD of about 0.029 to about 0.036 inches, and an ID of about 0.025 to about 0.030 inches. The inner tubular member 27 of the distal shaft section 19 has a length of about 25 to about 30 cm, typically about 28 cm, an OD of about 0.018 to about 0.025 inches, and an ID of about 0.014 to about 0.018 inches. The inner and outer tubular members 27/26 may taper in the distal section to a smaller OD or ID.

The balloon 14 may be formed of a variety of suitable compliant, semi- or non-compliant, or hybrid compliant materials depending on the use of the catheter, e.g., dilatation, stent delivery, etc. The length of the balloon 14 is typically about 10 to 50 mm, more specifically about 20 to 30 mm. In an expanded state, the balloon diameter is typically about 0.5 to about 4.5 mm, more specifically about 1.5 to about 4 mm. The wall thickness will vary depending on the burst pressure requirements and hoop strength of the balloon material.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A rapid exchange type balloon catheter, comprising:
   a) an elongated shaft having an inflation lumen and a guidewire lumen, and
      i) a proximal shaft section which defines a proximal portion of the inflation lumen, comprising a tubular member formed of polyetheretherketone having a proximal end and a distal end;
      ii) a distal shaft section comprising a first distal outer tubular member having a proximal end secured to the distal end of the polyetheretherketone tubular member, a second distal outer tubular member having a proximal end secured to a distal end of the first distal outer tubular member, and an inner tubular member disposed within the first and second distal outer tubular members and defining a guidewire lumen extending from a guidewire proximal port at a proximal end of the inner tubular member to a guidewire distal port at a distal end of the inner tubular member, the guidewire proximal port being formed by a side opening extending through a sidewall of the outer tubular member with a section of the inner tubular member in the side opening and fused to the sidewall of the outer tubular member; and
      iii) a fused shaft section having a length of about 1 millimeters to about 10 millimeters, formed by a portion of the first distal outer tubular member fused to an outer surface of the inner tubular member along a length thereof, the fused section extending from the proximal end of the inner tubular member to a location proximal to the second distal outer tubular member, with the inflation lumen extending along the fused section from the guidewire proximal port to the distal end of the fused section being defined by an inner surface of the first distal outer tubular member, the second distal outer tubular member having an inner surface, the inner surface extending around a circumference of the second distal outer tubular member and being spaced apart from the outer surface of the inner tubular member so that the inflation lumen in the second distal outer tubular member has an annular shape around the outer surface of the inner tubular member; and b) an inflatable balloon on the distal shaft section having a proximal end secured to the distal end of the second distal outer tubular member, a distal end secured to the inner tubular member, and an interior in fluid communication with the inflation lumen.

2. The balloon catheter of claim 1 wherein the first distal outer tubular member has an inner periphery with a first segment fused to part of an outer surface of the inner tubular member to form the fused section, and with a second segment which is not fused to the inner tubular member, so that the inflation lumen extending along the fused section distally from the guidewire proximal port is defined by the second segment of the inner periphery of the first outer tubular member and by a part of the outer surface of the inner tubular member not bonded to the first distal outer tubular member.

3. The balloon catheter of claim 2 wherein the length of the fused section is about 5 millimeters to about 7 millimeters in length.

* * * * *